| United States Patent [19] | [11] | 4,110,337 |
|---|---|---|
| Szarvasi | [45] | Aug. 29, 1978 |

[54] TRIAZOLOBENZODIAZEPINES

[75] Inventor: Etienne Szarvasi, Charbonnieres-les-Bains, France

[73] Assignee: Lipha, Lyonnaise Industrielle Pharmaceutique, Lyons, France

[21] Appl. No.: 449,477

[22] Filed: Mar. 8, 1974

[30] Foreign Application Priority Data

Mar. 9, 1973 [FR] France ................................. 73.08510
Oct. 4, 1973 [FR] France ................................. 73 35522
Nov. 22, 1973 [FR] France ................................. 73 41583

[51] Int. Cl.$^2$ .................... C07D 243/12; C07D 487/04
[52] U.S. Cl. ........................ 260/308 R; 260/239.3 B; 424/269; 260/465 E; 260/518 R; 260/518 A; 260/519

[58] Field of Search .................................... 260/308 R

[56] References Cited

U.S. PATENT DOCUMENTS 3,681,343  8/1972  Hester ............................. 260/308 R Primary Examiner—Alton D. Rollins
Attorney, Agent, or Firm—Browdy and Neimark

[57] ABSTRACT

A novel class of 4H-5,6-dihydro-[4,3-a]-s-triazolo-1,5-benzodiazepines is disclosed the members of which possess pharmacological activity, particularly analgesic or anti-inflammatory activity, likely to render them of value in the therapeutic field. Intermediates useful in the production of said class of compounds are also disclosed.

19 Claims, 42 Drawing Figures

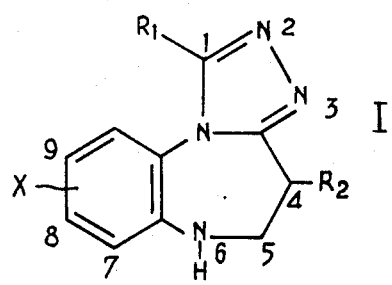 I
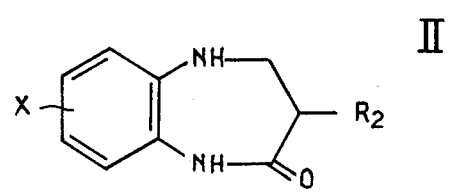 II
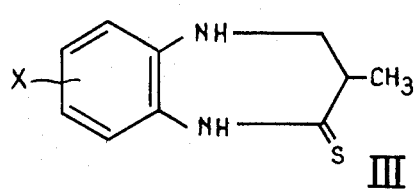 III
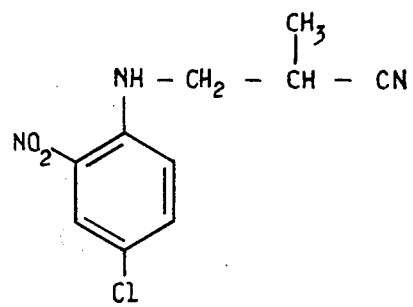 IV
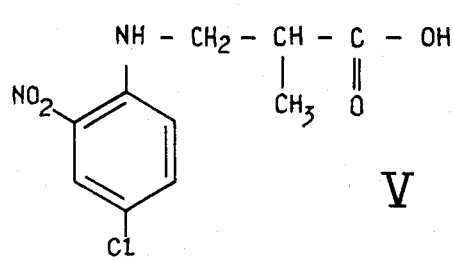 V
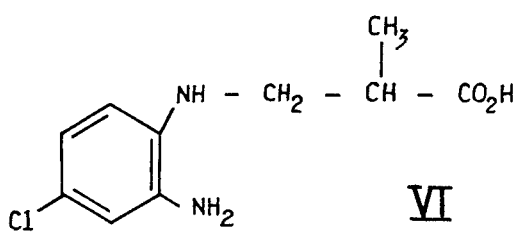 VI
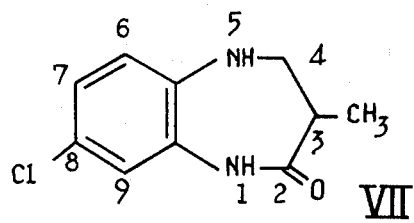 VII
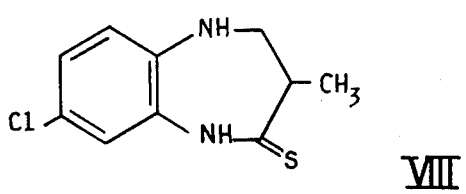 VIII
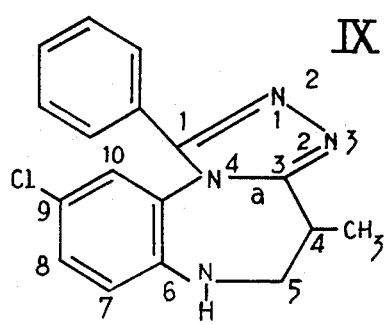 IX
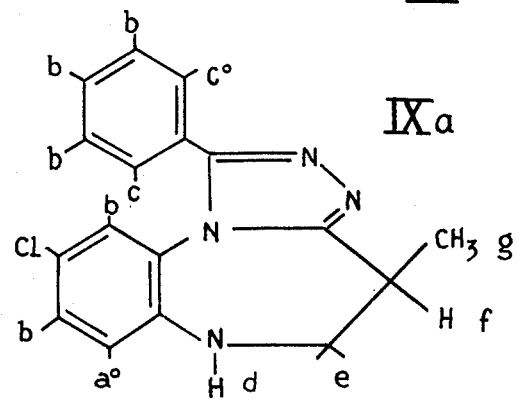 IXa

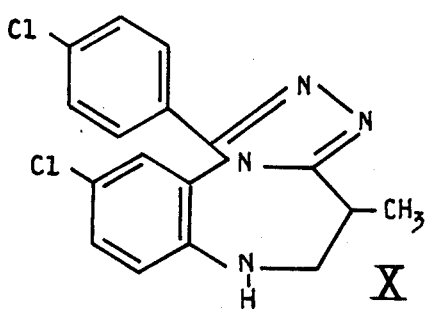
X
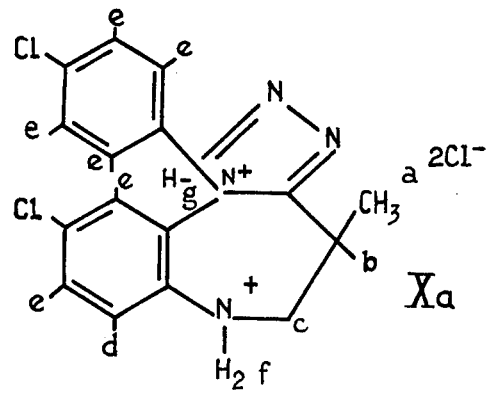
Xa
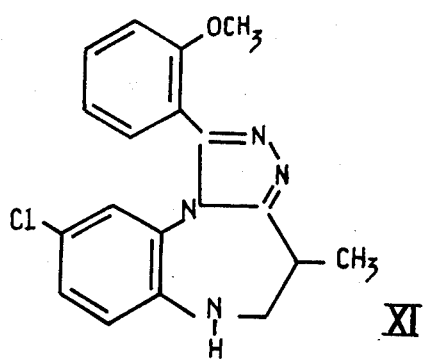
XI
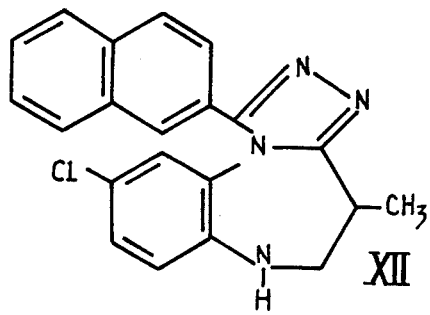
XII
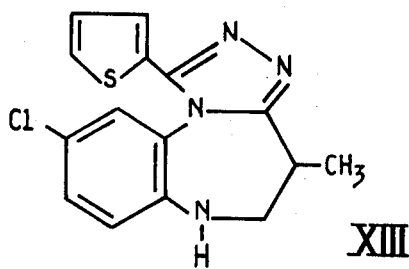
XIII
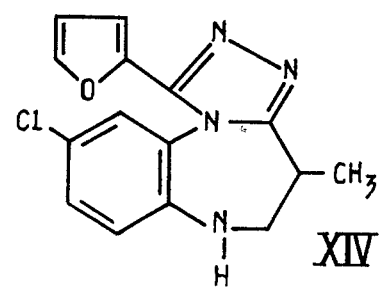
XIV
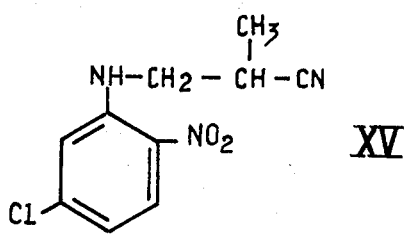
XV
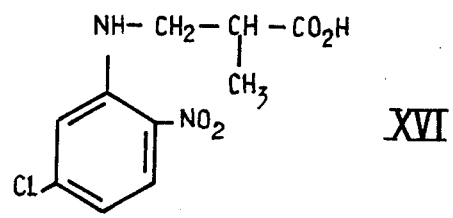
XVI
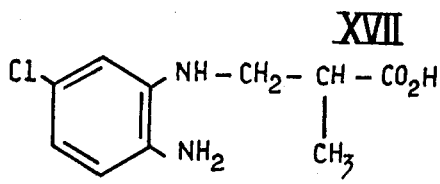
XVII
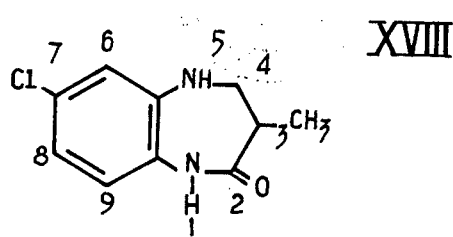
XVIII

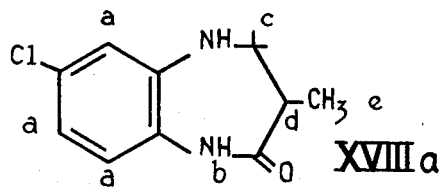 XVIIIa
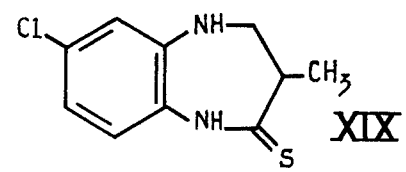 XIX
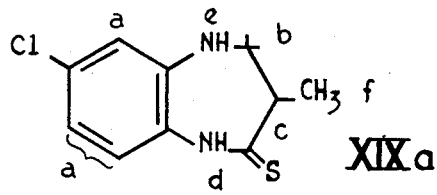 XIXa
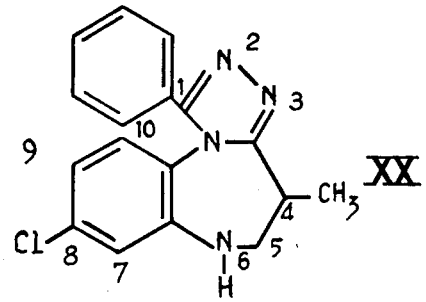 XX
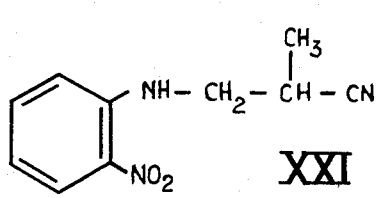 XXI
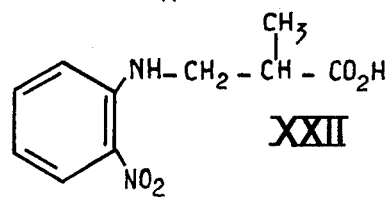 XXII
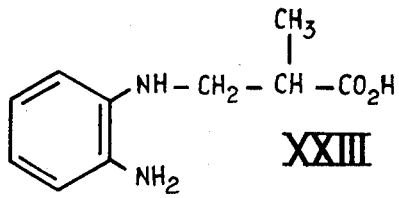 XXIII
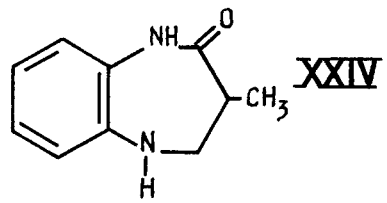 XXIV
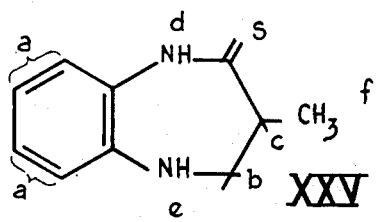 XXV
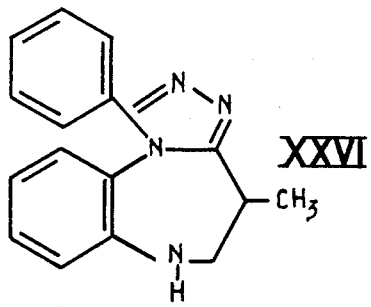 XXVI
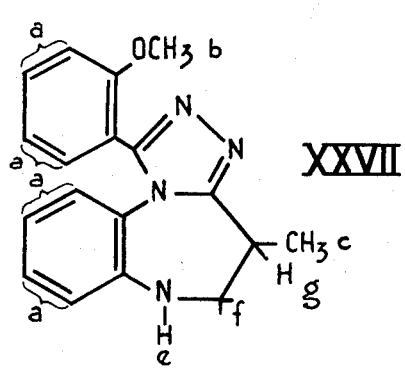 XXVII
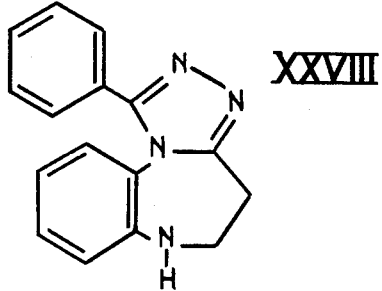 XXVIII

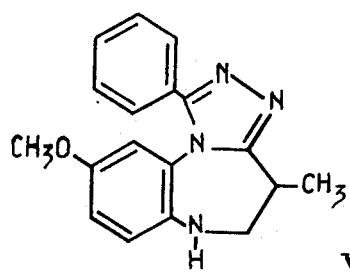 XXIX
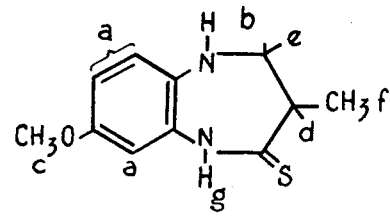 XXX
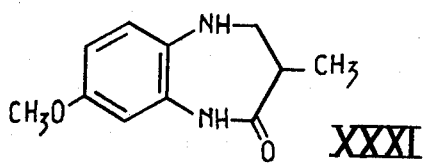 XXXI
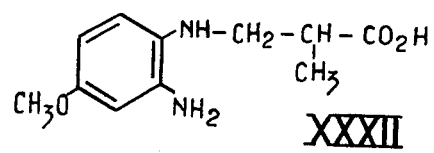 XXXII
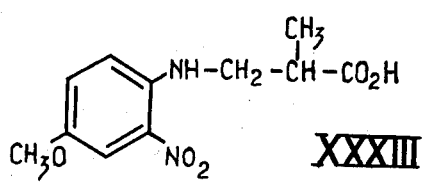 XXXIII
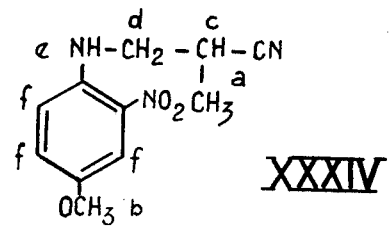 XXXIV
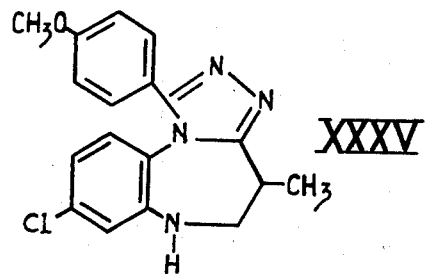 XXXV
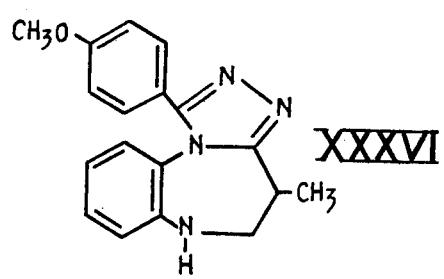 XXXVI
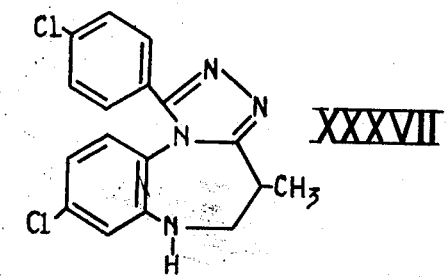 XXXVII
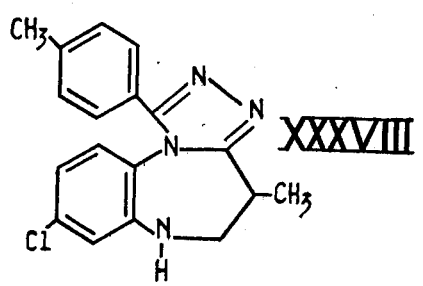 XXXVIII

TRIAZOLOBENZODIAZEPINES

FIELD OF THE INVENTION

This invention relates to new triazolobenzodiazepines and to a process for preparing them. It also relates to the use of these compounds in the field of therapeutics.

BACKGROUND OF THE INVENTION

Some [4,3-a]-s-triazolo-1,4-benzodiazepines, especially those substituted in the 6-position by phenyl, have been mentioned as having a pronounced effect on the central nervous system. Thus J-B Hester et al. (J. of Med. Chem. 1971, 1078–1081) have described a chemical series closely related to the substituted 5-phenyl-1,4-benzodiazepines previously studied by G. A. Archer and L. H. Sternbach (J. Org. Chem. 29, 231, 1964).

SUMMARY OF THE INVENTION

A new class of compounds has now been found possessing pharmacological activity and in particular analgesic or antiinflammatory activity whilst having substantially no tranquilising action on the central nervous system. The particular activity of these compounds is closely related to their structure and to the nature and position of the substituents present in the molecule.

DETAILED DESCRIPTION OF THE INVENTION

Thus in accordance with one aspect of the invention there is provided a novel class of 4H-5,6-dihydro-[4,3-a]-s-triazolo-1,5-benzodiazepines represented by the general formula:

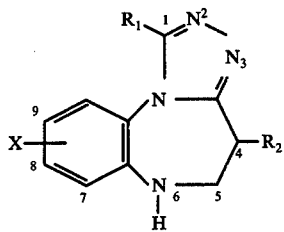

wherein X is hydrogen, a halogen atom in the 8- or 9-position, or a lower alkoxy group;

$R_1$ is a phenyl radical optionally substituted by a halogen atom or lower alkyl group in the para position or by a lower alkoxy group in the para or ortho position, a naphthyl radical, or a 2-furyl or 2-thienyl radical; and $R_2$ is hydrogen or a lower alkyl group.

One group of compounds falling within the class defined by formula I is that wherein X is hydrogen or a halogen atom in the 8- or 9-position; $R_1$ is a phenyl radical optionally substituted by a halogen atom or lower alkoxy group, a naphthyl radical, or a 2-furyl or 2-thienyl radical; and $R_2$ is a lower alkyl group.

Another group of compounds falling within the class defined by formula I is that wherein X is hydrogen, a halogen atom in the 8- or 9-position, or a lower alkoxy group; $R_1$ is a phenyl radical optionally substituted by a lower alkoxy group; and $R_2$ is hydrogen or a lower alkyl group.

A further group of compounds falling within the class defined by formula I is that wherein X is hydrogen or a chlorine atom in the 8-position; $R_1$ is a phenyl radical substituted in the para position by a chlorine atom or methyl or methoxy group; and $R_2$ is methyl.

The terms "lower alkyl group" and "lower alkoxy group" are used herein as meaning respectively an alkyl or alkoxy group containing from 1 to 4 carbon atoms, preferably methyl or methoxy.

In formula I, X is preferably hydrogen, chlorine or methoxy; $R_1$ is preferably an unsubstituted phenyl radical or a phenyl radical substituted by chlorine or a methyl or methoxy group, or a naphthyl, 2-furyl or 2-thienyl radical; and $R_2$ is preferably hydrogen or methyl.

The compounds of formula I can be prepared by a process comprising the following stages:

(a) reaction in a cyclic ether, for example tetrahydrofuran or dioxan, of a 2-nitroaniline of the general formula:

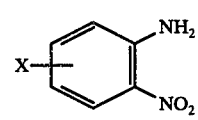

wherein X has the same meaning as in formula I, with a substituted acrylonitrile of the general formula

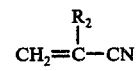

wherein $R^2$ has the same meaning as in formula I, in the presence of a base, for example trimethylbenzyl ammonium hydroxide or choline, to form a nitrile compound represented by the general formula:

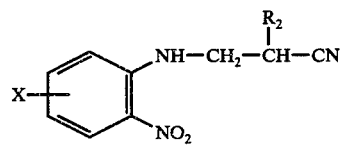

wherein X and $R_2$ have the same meanings as in formula I;

(b) acid hydrolysis of the nitrile compound of formula III, for example with aqueous sulphuric or acetic acid, to form a (2'-nitroanilino)-propionic acid represented by the general formula:

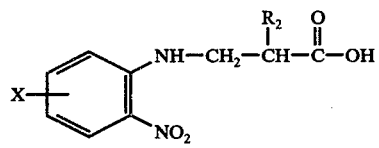

wherein X and $R_2$ have the same meanings as in formula I;

(c) hydrogenation of the acid of formula IV, for example with hydrogen and Raney nickel in tetrahydrofuran or palladium on charcoal in methanol or ethanol, to form a substituted propionic acid represented by the general formula:

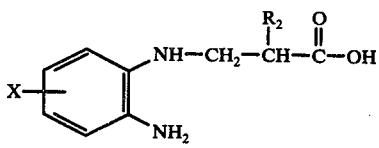

wherein X and $R_2$ have the same meanings as in formula I;

(d) reaction of the substituted propionic acid of formula V with polyphosphoric acid to form a benzodiazepine-2-one represented by the general formula:

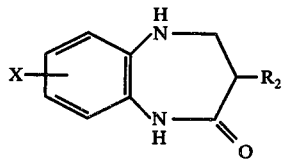

wherein X and $R_2$ have the same meanings as in formula I;

(e) reaction of the benzodiazepine-2-one of formula VI with phosphorus pentasulphide in the presence of pyridine or a chemical equivalent thereof to form the corresponding benzodiazepine-2-thione represented by the general formula:

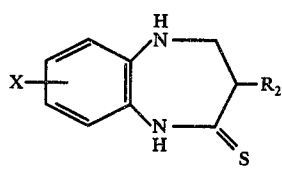

wherein X and $R_2$ have the same meanings as in formula I;

(f) reaction of the benzodiazepine-2-thione of formula VII with a hydrazide represented by the general formula:

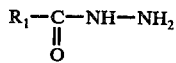

wherein $R_1$ has the same meaning as in formula I, to form the required triazolobenzodiazepine compound of formula I.

The 1H-2,3,4,5-tetrahydro-1,5-benzodiazepine-2-ones of formula VI in which $R_1$ is a lower alkyl group and the 1H-2,3,4,5-tetrahydro-1,5-benzodiazepine-2-thiones of formula VII in which $R_2$ is a lower alkyl group are believed to be novel compounds and as such form part of the present invention.

The compounds of formula I can be converted into the corresponding pharmaceutically acceptable acid addition salts by treatment with an appropriate acid, for example hydrochloric acid. All such salts are included within the scope of the present invention.

The triazolobenzodiazepines of formula I will normally be employed as therapeutic agents in the form of a pharmaceutical composition comprising as an essential active ingredient a compound of formula I in association with at least one pharmaceutical carrier therefor, which will normally be a diluent or excipient of the kind generally employed in the manufacture of medicaments ready for administration. The composition can be in a dosage unit form appropriate to the desired mode of administration, for example a tablet or capsule for oral administration.

EXAMPLES

The following Examples illustrate in a non-limiting manner the preparation of compounds in accordance with the invention. The pharmacological activities referred to in various of the Examples were determined as follows:

(1) The erythema with ultraviolet light on the guinea pig was determined by the method of C. V. Winder et al, Arch. Int. Pharmacodyn, 116, 261, 1958.

(2) The oedema to carragenine was determined by the method of C. A. Winter et al, Proc. Soc. Exp. Biol. med. 1962, 111, 544–7.

(3) The analgesic activity (acetic acid test) was determined by the method of R. Koster, Federation proc. 1959, 18, 412.

The standards used in the foregoing tests were:
For the analgesic test with acetic acid: acetylsalicylic acid. For the anti-inflammatory test - carragenine: phenyl butazone - U.V.: acetylsalicylic acid.

EXAMPLE 1

9-Chloro-4H-5,6-dihydro-4-methyl-1-phenyl-[4,3-a]-s-triazolo-1,5-benzodiazepine

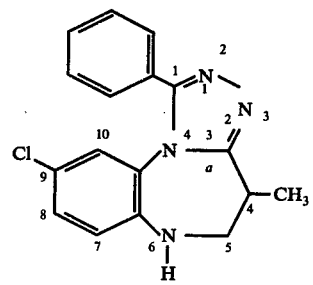

(a) 4'-Chloro-2'-nitro-N-(2-methyl-2-cyanoethyl)-aniline

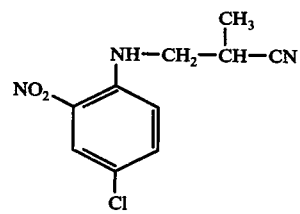

86.3 g (mol/2) of 4-chloro-2-nitroaniline are dissolved in 270 ml of tetrahydrofuran. 67 g (1 mol) of methacrylonitrile and 16 ml of a 40% solution in methanol of trimethylbenzyl ammonium hydroxide (sold commercially as "Triton B") are added. After heating under reflux for 6 hours and then evaporating the solvent, the solid residue is washed with water; 109.2 g of a brown solid, of melting point 76°–78° C., are collected. It still contains some of the aniline starting material. After recrystallisation from 1100 ml of ethanol, a product with a melting point of 110°–111° C. is obtained in a yield of 79.8 g = 66.6% (theoretical yield: 120 g).

(b) 2-Methyl-(4'-chloro-2'-nitroanilino)-propionic acid

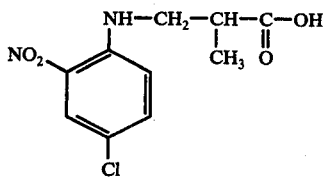

A solution is prepared of 60 ml of concentrated $H_2SO_4$ in 60 ml of water and 60 ml of acetic acid. To this solution are added 80 g (mol/3) of 4'-chloro-2'-nitro-N-(2-methyl-2-cyanoethyl)-aniline. After heating under reflux for 45 minutes, the reaction mixture is poured into water. After hydroextraction of the formed solid, this is dissolved in a 10% $Na_2CO_3$ solution. After filtration and washing with ethyl acetate, the solution made acid with HCl provides 67.4 g of a yellow solid. Yield: 78.2%; melting point = 162°-164° C. After recrystallisation (2 g in 30 ml of ethanol) m.p. = 163°-164° C.

(c) 2-Methyl-(2'-amino-4'-chloroanilino)-propionic acid

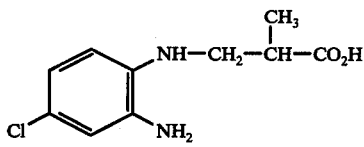

48 g (mol/5.36) of 2-methyl-(4'-chloro-2'-nitroanilino)-propionic acid, in 480 ml of tetrahydrofuran, are hydrogenated in the presence of 10 g of Raney nickel in a one-liter autoclave. $H_2$ pressure when cold: 135 kg. Pressure drop (calculated 24.5 kg - actual 30 kg). Temperature: 70°-90° C. Duration: 2½ hours.

After filtration of the catalyst and evaporation of the solvent, 44 g of a reddish brown solid are obtained and this is recrystallised from a mixture of alcohol and water (10:7) in the presence of decolorising carbon. A product with a melting point of 99° to 101° C. is obtained in a yield of 33.3 g = 78% (theoretical yield: 42.6 g). After being recrystallised twice from a mixture of alcohol and water, the melting point is 117°-118° C. (pink product).

(d) 8-Chloro-3-methyl-1H-2,3,4,5-tetrahydro-1,5-benzodiazepine-2-one

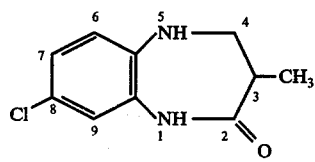

11.5 g (mol/20) of 2-methyl-(2'-amino-4'-chloranilino)-propionic acid, 140 ml of benzene, 10 ml of 85% orthophosphoric acid and 15.5 g of phosphorus pentoxide are heated under reflux for 45 minutes. The benzene layer is poured off, the oily residue is dissolved in water (external cooling), neutralisation is effected with dilute sodium hydroxide solution and the solid is extracted with water, washed with water and dried. A beige product with a melting point of 189°-191° C.is obtained in a yield of 9.1 g = 86.6% (theoretical yield: 10.5 g). After recrystallisation from 240 ml of ethyl acetate, a white product is obtained, m.p. = 195°-196° C.

(e) 8-Chloro-3-methyl-1H-2,3,4,5-tetrahydro-1,5-benzodiazepine-2-thione

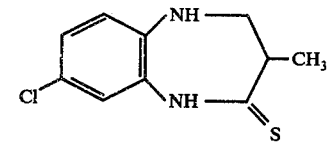

10.5 g (mol/20) of 8-chloro-3-methyl-1H-2,3,4,5-tetrahydro-1,5-benzodiazepine-2-one are dissolved in 50 ml of pyridine. 4.1 g (mol/100.8) of $P_4S_{10}$ are added (exothermic reaction; temperature from 28° C. to 40° C.). After heating under reflux for 40 minutes (the absence of CO is established by spectroscopy) the mixture is poured into iced water, extracted with water, washed with water and dried. A yellow product is obtained in a yield of 9.5 g = 84% (theoretical yield = 11.3 g), and the melting point is 186°-189° C.

After recrystallisation from 230 ml of ethanol, yellow needles are isolated, m.p. = 196°-197° C.

(f) 9-Chloro-4H-5,6-dihydro-4-methyl-1-phenyl- 4,3-a-s-triazolo-1,5-benzodiazepine 7.6 g (mol/30 ) of 8-chloro-3-methyl-1H-2,3,4,5-tetrahydro-1,5-benzodiazepine-2-thione and 5.5 g (mol/24.8) of benzoyl hydrazide are heated under nitrogen at a temperature of 140° C. for 10 minutes and 200° C. for 15 minutes until no more $H_2S$ is liberated and the formed water is eliminated. The molten mass is washed with water up to 95° C. and then with hexane. The water extracted solid is washed with a dilute sodium hydroxide solution, then with water and with ether and 10 g of a pink-coloured solid are obtained, m.p. = 175°-190° C. After recrystallization from 100 ml of isopropanol and decolorising carbon, white crystals having a melting point of 227°-228° C. are obtained in a yield of 5.8 g = 56% (theoretical yield = 10.3 g). After recrystallisation from ethyl acetate, the melting point is 228°-230° C.

It is also possible to prepare the same product in solution in 100 ml of boiling n-butanol (for the indicated quantities), under a nitrogen atmosphere for about 15 hours. Another variant consists in dissolving the reacting products in trimethylbenzene (substantially the same volume as previously) and to heat the resulting mixture under reflux while simultaneously distilling the trimethylbenzene-water azeotrope. The speed of distillation is regulated in such a way that the operation lasts from 45 minutes to 1 hour. It is advantageous to effect the synthesis by heating the reacting products to 250° C. under a nitrogen atmosphere for 45 minutes in a mixture of diphenyl ether and diphenyl. The yields are practically identical, whichever procedure is employed. Lethal dose 50 = $LD_{50}$ (mouse) (orally = P.O.) = 2400 mg/kg. Acetic acid test. Active dose 50 = $AD_{50}$ = 37 mg/kg.

EXAMPLE 2

9-Chloro-4H-5,6-dihydro-4-methyl-1-(4'-chlorophenyl)-[4,3-a]-s-triazolo-1,5-benzodiazepine In accordance with the working conditions of Example 1 (f), and using 6.8 g (mol/25) of 4-chlorobenzoyl hydrazide, and after recrystallisation of the crude product from alcohol, a white product is obtained in a yield of 7.4 g = 64% (theoretical yield = 11.5 g), melting point 211°–213° C. After a second recrystallisation from isopropanol, the melting point is 213°–214° C.

Dihydrochloride 3.45 g (mol/100) of the above base are dissolved in 180 ml of absolute methanol at a temperature of 30° C. Gaseous HCl is introduced thereinto at the same temperature to the point of saturation (4 g). The mixture is refrigerated. First pouring = 0.4 g, melting point 208°–212° C. According to the infrared spectrum, this is not the expected salt. The mother liquors, to which ether is added, yield a second pouring of 3.3 g of white product, melting point 217°–219° C. Yield = 3.3 g = 78.8% (theoretical yield = 4.2 g). After recrystallisation from ethanol and diisopropyl ether (2 : 1), the melting point is 222°–224° C. Acidity index A.I. (calculated: 267; found: 257).

EXAMPLE 3

9-Chloro-4H-5,6-dihydro-4-methyl-1-(o-methoxyphenyl)-[4,3-a]-s-triazolo-1,5-benzodiazepine The working conditions of Example 1 (f) are followed, starting with 11.3 g (mol/20) of 8-chloro-3-methyl-1H-2,3,4,5-tetrahydro-1,5-benzodiazepine-2-thione and 10 g (mol/16.6) of 2-methoxybenzoyl hydrazide. The crude product of the reaction is treated as in the aforementioned Example, except as regards the washing with hexane, which is replaced by washing with benzene. (The initial hydrazide has good solubility in benzene). In a yield of 13.4 g = 78.8% (theoretical yield = 17 g), a beige product with a melting point of 222°–224° C. is obtained. After recrystallisation from 230 ml of isopropanol, white crystals are isolated which have a melting point of 226°–227° C. $LD_{50}$ (mouse: P.O.) = > 3200 mg/kg. Acetic acid test: $AD_{50}$ = 24 mg/kg.

EXAMPLE 4

9-Chloro-4H-5,6-dihydro-1-(2'-naphthyl)-4-methyl-[4,3-a]-s-triazolo-1,5-benzodiazepine 11.3 g (mol/20) of 8-chloro-3-methyl-1H-2,3,4,5-tetrahydro-1,5-benzodiazepine-2-thione are dissolved in 100 ml of trimethyl benzene. 11.3 g (mol/16.5) of 2-naphthoyl hydrazide are added. The solution is heated under reflux, while simultaneously distilling the azeotrope of trimethyl benzene and water and then trimethyl benzene by itself. Total time = 45 minutes. During the heating, a strong release of $H_2S$ is observed. The solid residue is dispersed in water and then washed with sodium hydroxide and finally with ether. Yield: 13.2 g = 73.3% (theoretical yield: 18 g) of a beige product with a melting point of 200°–202° C. After recrystallisation from ethanol and decolorising carbon a white hygroscopic product of melting point 205°–206° C. is obtained. $LD_{50}$ (mouse: P.O.) = 3200 mg/kg. Acetic acid test: $AD_{50}$ = 67 mg/kg.

EXAMPLE 5

9-Chloro-4H-5,6-dihydro-4-methyl-(2'-thienyl)-[4,3-a]-s-triazolo-1,5-benzodiazepine Using the working conditions of Example 4 and starting with 7.6 g (mol/30 ≠) of 8-chloro-3-methyl-1H-2,3,4,5-tetrahydro-1,5-benzodiazepine-2-thione and 5.7 g (mol/24.8) of $N^1$-(2'-thenoyl)-hydrazide, 7.7 g of a grey product of melting point 197°–199° C. are obtained. After recrystallisation from 200 ml of ethyl acetate plus decolorising carbon, 5.3 g of white crystals of melting point 202°–202° C. are isolated. Yield (of pure product): 5.3 g = 50.4% (theoretical yield = 10.5 g), hygroscopic. Acetic acid test: $AD_{50}$ = 93 mg/kg.

EXAMPLE 6

9-Chloro-4H-5,6-dihydro-1-(2'-furyl)-4-methyl-[4,3-a]-s-triazolo-1,5-benzodiazepine Using the working conditions of Example 5 and starting with 5.1 g (mol/24.6) of 2-furoyl hydrazide, a product of melting point 192°–194° C. is obtained in a yield of 6.3 g = 63% (theoretical yield = 10 g). After recrystallisation from ethanol or ethyl acetate plus decolorising carbon, white crystals of melting point 197°–199° C are isolated. Acetic acid test: $AD_{50}$ = 60 mg/kg.

EXAMPLE 7

8-Chloro-4H-5,6-dihydro-4-methyl-1-phenyl-[4,3-a]-s-triazolo-1,5-benzodiazepine (a) 5'-Chloro-2-nitro-N-(2-methyl-2-cyanoethyl)-aniline 48.8 g (0.282 mol) of 5-chloro-2-nitroaniline are dissolved in 95 ml of tetrahydrofuran and 35 g (0.564 mol) of methacrylonitrile. The solution is heated to 30° C. and 9.9 ml of a 40% solution of "Triton B" in methanol are added dropwise. Heating takes place for 3 hours under reflux and then the tetrahydrofuran is evaporated. The pasty residue is dissolved with heat in 80 ml of ethanol. After heating under reflux for 10 minutes, cooling takes place overnight in a refrigerator, the product is water extracted, rinsed with isopropanol and then with hexane. After drying a yellow solid of melting point 110°–111° C. is collected in a yield of 39.3 g = 58.2%. Theoretical yield: 67.5 g. After recrystallisation from ethanol, the melting point is unchanged.

(b) 2-Methyl-(5'-chloro-2'-nitroanilino)-propionic acid

A mixture of 100 ml of water, 100 ml of sulphuric acid and 100 ml of crystallisable acetic acid is prepared and into this mixture are introduced 66.4 g (0.277 mol) of 5'-chloro-2'-nitro-N-(2-methyl-2-cyanoethyl)-aniline. Heating under reflux takes place at about 125° C. until a solid precipitates after about 2 hours. The solid is cooled and poured into iced water, and then water extracted. This solid, washed with water, is dissolved in a sodium carbonate solution. Any insoluble produce is eliminated, if necessary by filtration, and then acidification is carried out with concentrated HCl. A solid precipitates, and an extraction with ethyl acetate is carried out, and the organic layer is washed with water and dried over $Na_2SO_4$. The solvent is evaporated and an orange-coloured solid of melting point 159°–160° C. is collected in a yield of 63.3 g = 88.6%. Theoretical yield = 71.5 g. After recrystallisation from ethanol, the melting point is unchanged.

(c) 2-Methyl-(2'-amino-5'-chloranilino)-propionic acid

Using a one-liter autoclave, 53.4 g (0.206 mol) of 2-methyl-(5'-chloro-2'-nitroanilino)-propionic acid in solution in 500 ml of tetrahydrofuran are hydrogenated in the presence of 17 g of Raney nickel. Hydrogen pressure in the cold: 120 kg. Temperature 60° C. Duration: 1 hour. Pressure drop:
calculated 32 kg
found 45 kg. The catalyst is removed by filtration. The solvent is evaporated to dryness. The residue is dispersed in ether, water extracted and dried, and a pinky-beige solid of melting point 164°–165° C. is obtained in a yield of 38.9 g = 83%. Theoretical yield: 47 g. After recrystallisation from ethanol, the melting point is unchanged.

(d) 7-Chloro-3-methyl-1H-2,3,4,5-tetrahydro-1,5-benzodiazepine-2-one

A mixture is prepared from 280 ml of dry benzene, 31 g of phosphorus pentoxide and 20 ml of 85% orthophosphoric acid. 22.8 g (0.1 mol) of 2-methyl-(2'-amino-5'-chloranilino)-propionic acid are introduced. Heating under reflux takes place for half an hour and the benzene is eliminated by decantation after the mixture has been cooled. The residue is taken up in water and made alkaline with 30% NaOH to pH 7–8.

The precipitate obtained is water extracted, thoroughly washed with water and then with hexane and dried. A greyish solid of melting point 163°–165° C. is obtained in a yield of 19.8 g = 94.3%. Theoretical yield = 21 g. After recrystallisation from ethanol, the melting point is 165°–167° C.

(e) 7-Chloro-3-methyl-1H-2,3,4,5-tetrahydro-1,5-benzodiazepine-2-thione 41 g (0.193 mol) of 7-chloro-3-methyl-1H-2,3,4,5-tetrahydro-1,5-benzodiazepine-2-one are dissolved in 194 ml of pyridine. 16.2 g (0.038 mol) of phosphorus pentasulphide ($P_4S_{10}$) are introduced in small portions. Refluxing takes place for 40 minutes; after cooling, the product is poured into about 1 liter of a mixture of water and ice. A product crystallises, which is water extracted and thoroughly washed with water and then with hexane. After drying, a yellowish solid of melting point 160°–162° C. is obtained in a yield of 32.7 g = 74.4%. Theoretical yield = 44 g. After recrystallisation from ethanol, the melting point is unchanged.

(f) 8-Chloro-4H-5,6-dihydro-4-methyl-1-phenyl-[4,3-a]-s-triazolo-1,5-benzodiazepine 7.6 g (mol/30) of 7-chloro-3-methyl-1H-2,3,4,5-tetrahydro-1,5-benzodiazepine-2-thione and 5.5 g (mol/25) of benzoyl hydrazide are dissolved at 110° C. in 120 ml of trimethyl benzene. The solvent and the formed water are distilled over ¾ hour. The last traces are driven off by evaporation under vacuum. Cooling takes place. The residue is dispersed in ether, water extracted, washed with a dilute sodium hydroxide solution and then with water. The product is rinsed with hexane and then with ether and dried. 8.3 g of a beige-coloured solid of melting point 213°–216° C. are obtained. Yield = 8.3 g = 80% (theoretical yield = 10.3 g). After recrystallisation from ethyl acetate in the presence of decolorising carbon, the melting point is 220°–222° C. Analgesic test with acetic acid: $AD_{50} = 8.75$ mg/kg Anti-inflammatory test: (a) carragenine: $AD_{50} = 62$ mg/kg; (b) U.V. : minimal active dose 75 mg/kg. Antipyretic test: $AD_{50} = 25.4$ mg/kg.

EXAMPLE 8

4H-5,6-Dihydro-4-methyl-1-phenyl-[4,3-a]-s-triazolo-1,5-benzodiazepine

(a) 2-Nitro-(2'-methyl-2'-cyanoethyl)-aniline 69 g (mol/2) of o-nitroaniline in solution in 270 ml of tetrahydrofuran are heated under reflux for 2 hours with 67 g (1 mol) of methacrylonitrile and 16 ml of a 40% solution of "Triton B" in methanol. After evaporation of the volatile substances under vacuum, washing the residue with water and then extraction with ethyl acetate, and after evaporation of the solvent, a yellow solid of melting point 44°–47° C. is obtained in a yield of 51.3 g = 50% (theoretical yield: 102.6 g). After recrystallisation from isopropanol and then from ethanol, there is obtained a yellow product of melting point 75°–76° C.

(b) 2-Methyl-(2'-nitroanilino)-propionic acid 41.2 g (mol/5) of 2-nitro-(2'-methyl-2'-cyanoethyl)-aniline, 36 ml of water, 36 ml of sulphuric acid and 36 ml of acetic acid are heated under reflux for 45 minutes. The reaction mixture is poured into iced water. After water extraction and washing, followed by dissolving in an $Na_2CO_3$ solution, the resulting alkali solution is washed with ethyl acetate and is then acidified with hydrochloric acid. The precipitate which forms is water extracted. A yellow product of melting point 132°–133° C. is obtained in a yield of 31.6 g = 70.5% (theoretical yield: 44.8 g). After recrystallisation from ethanol, the melting point is unchanged.

(c) 2-Methyl-(2'-aminoanilino)-propionic acid 30 g (mol/7.45) of 2-methyl-(2'-nitroanilino)-propionic acid in solution in 320 ml of methanol are hydrogenated in the presence of 3 g of palladium on carbon to 10% in an autoclave with a capacity of 500 ml. $H_2$ pressure in the cold = 105 kg/cm². Temperature = 25°–35° C. (exothermic). Duration: 5 minutes. Pressure drop (calculated): 53 kg (actual): 43 kg. After filtration of the catalyst and evaporation of the filtrate to dryness, 22 g of a pink-coloured solid of melting point 130°–132° C. are isolated. Yield 84.6% (theoretical yield = 26 g).

After recrystallisation from ethanol-water (1 : 1), the melting point is 134°–135° C.

(d) 3-Methyl-1H-2,3,4,5-tetrahydro-1,5-benzodiazepine-2-one 38.9 g (mol/5 = 38.84 g) of 2-methyl-(2'-aminoanilino)-propionic acid are heated under reflux with 560 ml of benzene, 40 ml of 85% orthophosphoric acid and 62 g of phosphorus pentoxide. The treatment yields 29.8 g of a beige-coloured solid of melting point 196°–197° C. in a yield of 84.6% (theoretical yield = 35.2 g). After recrystallisation from ethanol, the melting point of the resulting white solid is 202° C. to 202° C.

(e) 3-Methyl-1H-2,3,4,5-tetrahydro-1,5-benzodiazepine-2-thione 23 g (mol/7.7) of 3-methyl-1H-2,3,4,5-tetrahydro-1,5-benzodiazepine-2-one are dissolved at 90° C. in 150 ml of pyridine. 10.6 g (mol/41.6) of phosphorus pentasulphide are added. The mixture is heated under reflux for 40 minutes. The treatment yields 18.2 g of a yellow solid with a melting point of 193°–195° C., in a yield of 72.7% (theoretical yield = 24.9 g). After recrystallisation from ethanol, the melting point is 194°–195° C.

(f)
4H-5,6-dihydro-4-methyl-1-phenyl-[4,3-a]-s-triazolo-1,5-benzodiazepine 6.4 g (mol/30) of 3-methyl-1H-2,3,4,5-tetrahydro-1,5-benzodiazepine-2-thone, 5.5 g (mol/24.8) of benzoyl hydrazide and 100 ml of trimethyl benzene are heated under reflux, while simultaneously distilling the solvent and the water formed in the reaction. The residue is washed with ether, with a sodium hydroxide solution, with water and is then dried. A beige-coloured product of melting point 229°–231° C. (softening at 226° C.) is obtained in a yield of 6.8 g = 73.9% (theoretical yield = 9.2 g). After being recrystallised twice from ethanol plus water plus carbon, the melting point of the white solid is 239°–240° C. Analgesic test with acetic acid: $AD_{50}$ = 6 mg/kg. Anti-inflammatory test: with carragenine: $AD_{30}$ = 62 mg/kg with ultraviolet, minimal active dose: 9 mg/kg.

EXAMPLE 9

4H-5,6-Dihydro-4-methyl-1-(o-methoxyphenyl)-[4,3-a]-s-triazolo-1,5-benzodiazepine Following the conditions of Example 8 (f) and starting with 6.4 g (mol/30) of 3-methyl-1H-2,3,4,5-tetrahydro-1,5-benzodiazepine-2-thione, a crude product is obtained which, after being recrystallised from isopropanol, yields 4.4 g of substantially white crystals with a melting point of 223°–225° C. Yield: 4.4 g = 43.4% (theoretical yield = 10.15 g). After being further recrystallised from ethanol, a white product having a melting point of 228° C. to 230° C. is obtained.

Pharmacology $LD_{50}$ (mouse; P.O.) = > 3200 mg/kg
Analogesic test (acetic acid): $AD_{50}$ = 14 mg/kg (active dose 50).
Anti-inflammatory test: carragenine coefficient = 85 U.V. coefficient = 40.
It is established that this product is more active than its analogue chlorinated in the 9-position as previously described.

EXAMPLE 10

4H-5,6-Dihydro-1-phenyl-[4,3-a]-s-triazolo-1,5-benzodiazepine

The procedure of Example 9 is followed, starting with 5.9 g (mol/30) of 1H-2,3,4,5-tetrahydro-1,5-benzodiazepine-2-thione.
The residue obtained is dispersed in water and then rinsed with hexane, and after recrystallisation from ethyl acetate (ACOEt), yields 4 g of a white product having a melting point of 175°–177° C. Yield 4 g = 46% (theoretical yield: 8.74 g). After further recrystallisation from ethyl acetate, the melting point of the white product is 183°–185° C.

Pharmacology $LD_{50}$ (mouse; P.O.) = 1200 mg/kg
Analgesic test (acetic acid): $AD_{50}$ = 4 mg/kg
Anti-inflammatory test: carragenine $AD_{30}$ = 62.5 mg/kg U.V.: minimal active dose: 37.5 mg/kg.

This product is more active than its analogue methylated in the 4-position as previously described. On the other hand, it is twice as toxic.

EXAMPLE 11

4H-5,6-Dihydro-9-methoxy-4-methyl-1-phenyl-[4,3-a]-s-triazolo-1,5-benzodiazepine The procedure of Example 10 is followed, starting with 7.4 g (mol/30) of 8-methoxy-3-methyl-1H-2,3,4,5-tetrahydro-1,5-benzodiazepine-2-thione and 5.5 g (mol/24.8) of benzoyl hydrazide in 100 ml of trimethylbenzene. The treatment yields 8.3 g of a beige-coloured solid of melting point 213°–216° C., which is recrystallised from 80 cc of isopropanol. Yield = 4.9 g = 48% (theoretical yield = 10.2 g). Melting point: 224°–226° C. After recrystallisation from isopropanol, a substantially white product is obtained with a melting point of 230°–231° C.

Pharmacology $LD_{50}$ (mouse; P.O.) = 1000 mg/kg
Analgesic test (acetic acid): $AD_{50}$ = 8.3 mg/kg
Anti-inflammatory test: carragenine: $AD_{30}$ = 79 mg/kg U.V. minimal active dose = 62.5 mg/kg.
This product is to be compared with its analogue as described in Example 9. Its biological effect is greater, but it is more toxic.

EXAMPLE 12

8-Chloro-4H-5,6-dihydro-4-methyl-1-(p-methoxyphenyl)-[4,3-a]-s-triazolo-1,5-benzodiazepine 11.3 g (mol/20) of 7-chloro-3-methyl-1H-2,3,4,5-tetrahydro-1,5-benzodiazepine-2-thione (prepared as described in Example 7 (e)) are heated under reflux with 10 g (mol/16.6) of 4-methoxybenzoyl hydrazide, while simultaneously distilling off the water formed in the reaction. The operation lasts 90 minutes, during which there is a strong release of $H_2S$. The residue is dispersed beneath a layer of ether and it is water extracted, washed with dilute sodium hydroxide, then several times with hot water and rinsed with hexane. 10 g of product are obtained with a melting point of 190°–201° C. (softening at 160° C.), in a yield of 58.8% (theoretical yield 17 g). After recrystallisation from isopropanol, the melting point is 203°–204° C.

Pharmacology

Lethal dose 50 $LD_{50}$ (mouse = 2320 mg/kg (P.O.)
Analgesic activity (acetic acid test)
Active dose 50 $AD_{50}$ = 5.8 mg/kg
Anti-inflammatory activity (carragenine: $AD_{30}$ = 90 mg/kg) (U.V.: M.A.D. (minimal active dose) = 75 mg/kg).

EXAMPLE 13

4H-5,6-Dihydro-4-methyl-1-(p-methoxyphenyl-[4,3-a]-s-triazolo-1,5-benzodiazepine Complying with the conditions of Example 12 and starting with 6.4 g (mol/30) of 3-methyl-1H-2,3,4,5-tetrahydro-1,5-benzodiazepine-2-thione and 6.7 g of 4-methoxybenzoyl hydrazide, the resulting residue when treated with boiling water yields 6 g of a beige solid with a melting point of 209°–211° C. (softening at 190° C.). After recrystallisation from isopropanol, 3.8 g of beige product of melting point 231°–233° C. are obtained, the yield (of pure product) being 37% (theoretical yield 10.2 g). After once again recrystallising from isopropanol, the melting point is 232°-234° C.

Pharmacology

LD$_{50}$(mouse) = 650 mg/kg
Analgesia AD$_{50}$ = 2.8 mg/kg
Anti-inflammatory effect (carragenine: AD$_{30}$ = 90 mg/kg) (U.V.: M.A.D. = 75 mg/kg).

EXAMPLE 14

8-Chloro-4H-5,6-dihydro-4-methyl-1-(p-chlorophenyl)-[4,3-a]-s-triazolo-1,5-benzodiazepine According to Example 12, starting with 7.6 g (mol/30) of 7-chloro-3-methyl-1H-2,3,4,5-tetrahydro-1,5-benzodiazepine-2-thione and 6.8 g (mol/25) of p-chlorobenzoyl hydrazide, 8 g of product of melting point 236°-238° C. are obtained, in a yield of 69.5% (theoretical yield = 11.5 g). After being recrystallised from ethyl alcohol in the presence of decolorising carbon, a white solid of melting point 240°-242° C. is obtained.

Pharmacology

LD$_{50}$ = 3200 mg/kg
Analgesia AD$_{50}$ = 49 mg/kg
Anti-inflammatory effect: inactive.

EXAMPLE 15

8-Chloro-4H-5,6-dihydro-4-methyl-1-(p-tolyl)-[4,3-a]-s-triazolo-1,5-benzodiazepine According to Example 12, starting with 7.6 g (mol/30) of 7-chloro-3-methyl-1H-2,3,4,5-tetrahydro-1,5-benzodiazepine-2-thione and 6 g (mol/25) of p-tolyl hydrazide, 8.3 g of product with a melting point of 239°-241° C. are obtained in a yield of 76.5% (theoretical yield = 10.8 g); after recrystallisation from ethyl alcohol in the presence of decoloring carbon, the melting point is 244°-246° C.

Pharmacology

LD$_{50}$(mouse) = > 3200 mg/kg (P.O.)
Analgesia AD$_{50}$ = 66 mg/kg
Anti-inflammatory effect: inactive.

EXAMPLE 16

(a) 2-Nitro-4-methoxy-(2'-methyl-2'-cyanoethyl)-aniline 84 g (mol/2) of 2-nitroanisidine (also called 3-p-nitroanisidine) are dissolved while luke warm in 370 ml of tetrahydrofuran. Added to the solution are 67 g (1 mol) of methacrylonitrile and 16 cc of a 40% solution of "Triton B" in methanol. Heating under reflux: 3 hours. After cooling, the product crystallises. The mixture is left in a refrigerator overnight. Yield: 62.9 g = 53.4% (theoretical yield = 117.6 g), red product, m.p. = 114°-115° C. After recrystallisation (ethanol plus decolorising carbon), melting point 116°-117° C., orange-coloured product.

(b) 2-Methyl-(2'-nitro-4'-methoxyanilino)-propionic acid 47 g (mol/5 ≠) of 2-nitro-4-methoxy-(2'-methyl-2'-cyanoethyl)-aniline, 36 ml of H$_2$O, 36 ml of acetic acid and 36 ml of H$_2$SO$_4$ are heated under reflux for 25 minutes. The reaction mixture is poured into iced water and is made alkaline with an Na$_2$CO$_3$ solution. 4.5 G of solid are eliminated by filtration. The solution is washed first of all with ethyl acetate and then acidified. The formed crystals are water extracted. Yield: 23.8 g = 47.7% (theoretical yield = 50.8 g) of a deep red solid of melting point 119°-121° C. After recrystallisation (ethylacetate plus decoloring carbon) a red solid, m.p. = 124°-126° C. is obtained.

(c) 2-Methyl-(2'-amino-4'-methoxyanilino)-propionic acid 32.6 g (mol/7.8) of 2-methyl-(2'-nitro-4'-methoxyanilino)-propionic acid, in solution in 330 ml of tetrahydrofuran, are hydrogenated in the presence of 20 g of Raney nickel in an autoclave with a capacity of 500 ml. Hydrogen pressure in the cold: 150 kg/cm$^2$. Temperature = 70°-90° C.; Duration: 3 hours

| Pressure drop | calculated = 68 kg |
| | actual = 30 kg |

After filtration of the catalyst and evaporation of the solvent, an amorphous brown product is obtained, which is used as such.

(d) 3-Methyl-8-methoxy-1H-2,3,4,5-tetrahydro-1,5-benzodiazepine-2-one

The crude 2methyl-(2'-amino-4'-methoxyanilino)-propionic acid obtained in (c) above, 296 ml of benzene, 21 ml of ET H$_3$PO$_4$ and 33 g of P$_2$O$_5$ are heated under reflux for 45 minutes. The treatment yields 20.6 g of beige-coloured solid of melting point 141°-143° C. Yield = 50% (theoretical yield = 41.24 g, calculated on the acid). After recrystallisation from ethanol plus decolorising carbon, a pale beige product of melting point 142°-143° C. is obtained.

(e) 3-Methyl-8-methoxy-1H-2,3,4,5-tetrahydro-1,5-benzodiazepine-2-thione 10.3 G (mol/20) of 3-methyl-8-methoxy-1H-2,3,4,5-tetrahydro-1,5-benzodiazepine-2-one, in solution in 50 ml of pyridine, with 4.1 g (mol/100.8) of P$_4$S$_{10}$, are heated for 40 minutes. The mixture which is obtained, poured onto ice, leaves 8.9 g of yellow product of melting point 133°-136° C. (with softening at 125° C.). After being recrystallised three times from isopropanol plus ethanol plus decolorising carbon, the melting point is 144°-145.5° C.

I claim:

1. 4H-5,6-dihydro-[4,3-a]-s-triazolo-1,5-benzodiazepines represented by the general formula:

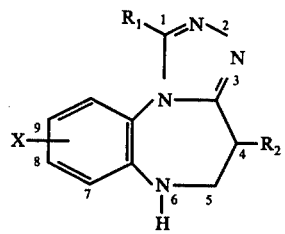

and pharmaceutically acceptable acid addition salts thereof, wherein X is hydrogen, a halogen atom in the 8- or 9-position, or a lower alkoxy group; R$_1$ is a phenyl radical optionally substituted by a halogen atom or lower alkyl group in the para position or by a lower alkoxy group in the para or ortho position, a naphthyl radical, or a 2-furyl or 2-thienyl radical; and $R_2$ is hydrogen or a lower alkyl group.

2. Triazolobenzodiazepines as claimed in claim 1, wherein X is hydrogen or a halogen atom in the 8- or 9-position; $R_1$ is a phenyl radical optionally substituted by a halogen atom or lower alkoxy group, a naphthyl radical, or a 2-furyl or 2-thienyl radical; and $R_2$ is a lower alkyl group.

3. Triazolobenzodiazepines as claimed in claim 1, wherein X is hydrogen, a halogen atom in the 8- 9-position, or a lower alkoxy group; $R_1$ is a phenyl radical optionally substituted by a lower alkoxy group; and $R_2$ is hydrogen or a lower alkyl group.

4. Triazolobenzodiazepines as claimed in claim 1, wherein X is hydrogen or a chlorine atom in the 8-position; $R_1$ is a phenyl radical substituted in the para position by a chlorine atom or methyl or methoxy group; and $R_2$ is methyl.

5. A compound in accordance with claim 1 which is 9-Chloro-4H-5,6-dihydro-4-methyl-1-phenyl-[4,3-a]-s-triazolo-1,5-benzodiazepine.

6. A compound in accordance with claim 1 which is 9-Chloro-4H-5,6-dihydro-4-methyl-1-(4'-chlorophenyl)-[4,3-a]-s-triazolo-1,5-benzodiazepine.

7. A compound in accordance with claim 1, which is 9-Chloro-4H-5,6-dihydro-4-methyl-1-(o-methoxyphenyl)-[4,3-a]-s-triazolo-1,5-benzodiazepine.

8. A compound in accordance with claim 1 which is 9-Chloro-4H-5,6-dihydro-1-(2'-naphthyl)-4-methyl-[4,3-a]-s-triazolo-1,5-benzodiazepine.

9. A compound in accordance with claim 1 which is 9-Chloro-4H-5,6-dihydro-4-methyl-(2'-thienyl)-[4,3-a]-s-triazolo-1,5-benzodiazepine.

10. A compound in accordance with claim 1 which is 9-Chloro-4H-5,6-dihydro-1-(2'-furyl)-4-methyl-[4,3-a]-s-triazolo-1,5-benzodiazepine.

11. A compound in accordance with claim 1 which is 8-Chloro-4H-5,6-dihydro-4-methyl-1-phenyl-[4,3-a]-s-triazolo-1,5-benzodiazepine.

12. A compound in accordance with claim 1 which is 4H-5,6-Dihydro-4-methyl-1-phenyl-[4,3-a]-s-triazolo-1,5-benzodiazepine.

13. A compound in accordance with claim 1 which is 4H-5,6-Dihydro-4-methyl-1-(o-methoxyphenyl)-[4,3-a]-s-triazolo-1,5-benzodiazepine.

14. A compound in accordance with claim 1 which is 4H-5,6-Dihydro-1phenyl-[4,3-a]-s-triazolo-1,5-benzodiazepine.

15. A compound in accordance wth claim 1 which is 4H-5,6-Dihydro-9-methoxy-4-methyl-1-phenyl-[4,3-a]-s-triazolo-1,5-benzodiazepine.

16. A compound in accordance with claim 1 which is 8-Chloro-4H-5,6-dihydro-4-methyl-1-(p-methoxyphenyl)-[4,3-a]-s-triazolo-1,5-benzodiazepine.

17. A compound in accordance with claim 1 which is 4H-5,6-Dihydro-4-methyl-1-(p-methoxyphenyl-[4,3-a]-s-triazolo-1,5-benzodiazepine.

18. A compound in accordance with claim 1 which is 8-Chloro-4H-5,6-dihydro-4-methyl-1-(p-chlorophenyl)-[4,3-a]-s-triazolo-1,5-benzodiazepine.

19. A compound in accordance with claim 1 which is 8-Chloro-4H-5,6-dihydro-4-methyl-1-(p-tolyl)-[4,3-a]-s-triazolo-1,5-benzodiazepine.

* * * * *